United States Patent [19]
Cordi et al.

[11] Patent Number: 5,385,920
[45] Date of Patent: Jan. 31, 1995

[54] DIACYLGLYCEROL NICOTINATES

[75] Inventors: Alex Cordi, Suresnes; Jean-Michel Lacoste, Sevres; Jacques Duhault, Croissy sur Seine; Joseph Espinal, Paris; Michelle Boulanger, Chatou, all of France

[73] Assignee: Adir et Compagnie, Courbevoie, France

[21] Appl. No.: 73,894

[22] Filed: Jun. 9, 1993

[30] Foreign Application Priority Data

Jun. 10, 1992 [FR] France ................... 92 06951

[51] Int. Cl.6 ................... A61K 31/44; C07D 213/02
[52] U.S. Cl. ................... 514/356; 514/255; 544/406; 546/318
[58] Field of Search ................... 546/318; 544/406; 514/255, 356

[56] References Cited

PUBLICATIONS

J. Pharmacobio–Dyn. 11, 555–562 (1988).

Chemical Abstract, vol. 102, No. 7, Abstract No. 67,401z, p. 337, Feb. 18, 1985.

*Primary Examiner*—C. Warren Ivy
*Assistant Examiner*—Zinna N. Davis
*Attorney, Agent, or Firm*—Gordon W. Hueschen

[57] ABSTRACT

Compounds of formula (I):

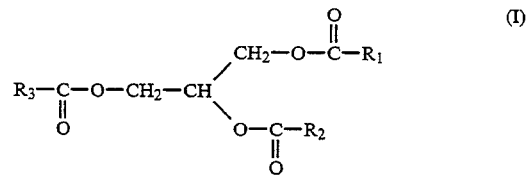

in which:

$R_1$ and $R_2$, which are identical or different, represent a higher alkyl or higher alkenyl radical,
$R_3$ represents a pyridyl or pyrazinyl radical, their isomers and their addition salts with a pharmaceutically acceptable acid and medicaments for the reduction of plasma lipids containing the same.

7 Claims, 3 Drawing Sheets

DIACYLGLYCEROL NICOTINATES

The present invention relates to new diacylglycerol nicotinates. Certain diacylglycerol nicotinates have already been described, especially by J. Sugihara et al. (J. Pharmacobio-Dyn., 11, 555–562 (1988)). These compounds are used for correcting the rise in plasma lipid levels, in particular LDL cholesterol and triglycerides. However, the compounds described by J. Sugihara are used in significant doses in order to overcome their brevity of action. This leads to high plasma concentrations which are responsible for a peripheral vasodilation causing "flush" and pruritus. Moreover, the hypolipemic effect, which lasts approximately 4 hours, is followed by a significant resurgence. The new diacylglycerol nicotinates described in the present application were synthesized with the aim of avoiding a rapid absorption leading to the "flush" effect and of obtaining lower and more long-lasting plasma concentrations which avoid the resurgence phenomenon.

More specifically, the present invention relates to new diacylglycerol nicotinates of formula (I):

$$R_3-C(=O)-O-CH_2-CH\big(CH_2-O-C(=O)-R_1\big)\big(O-C(=O)-R_2\big) \quad (I)$$

in which: $R_1$ and $R_2$, which are identical or different, represent a linear or branched ($C_{11}$–$C_{19}$) alkyl or linear or branched ($C_{11}$–$C_{19}$) alkenyl radical, $R_3$ represents a 3-pyridyl, 2-methyl-5-pyrazinyl or 2-methyl-5-pyrazinyl N-oxide radical, to their enantiomers and optional diastereoisomers, and to their addition salts with a pharmaceutically acceptable acid.

Among the pharmaceutically acceptable acids, there may be mentioned, in a non-limiting manner, hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric acids and the like.

The invention also applies to the process for the preparation of the compounds of formula (I), wherein the 1,3-dioxolane of formula (II), in the racemic form or the form of a pure enantiomer:

$$\begin{bmatrix} -O \\ -O \end{bmatrix}\!\!>\!\!< \qquad (II)$$
$$CH_2-OH$$

is reacted with the acid chloride of formula (III):

$$R'_3-CO-Cl \qquad (III)$$

in which $R'_3$ represents a 3-pyridyl or 2-methyl-5-pyrazinyl radical, to lead to the 1,3-dioxolane of formula (IV):

$$\begin{bmatrix} -O \\ -O \end{bmatrix}\!\!>\!\!< \qquad (IV)$$
$$CH_2-O-C(=O)-R'_3$$

in which $R'_3$ has the same meaning as above, which is converted to the corresponding diol of formula (V), in acid medium:

$$\begin{bmatrix} -OH \\ -OH \\ -O-C(=O)-R'_3 \end{bmatrix} \qquad (V)$$

in which $R'_3$ has the same meaning as above, which, depending on the nature of the compounds of formula (I) which it is desired to obtain, is reacted with:
either, in the case where $R_1$ and $R_2$ are identical:
2 equivalents of the acid chloride of formula (VI), in the presence of a base, $$R_1-CO-Cl \qquad (VI)$$

in which $R_1$ has the same meaning as in formula (I), to lead to the compound of formula (I/a), a particular case of the compounds of formula (I), $$\begin{bmatrix} -O-CO-R_1 \\ -O-CO-R_1 \\ -O-CO-R'_3 \end{bmatrix} \qquad (I/a)$$

in which $R_1$ and $R'_3$ have the same meaning as above, or, in the case where $R_1$ and $R_2$ are different:
with one equivalent of the acid chloride of formula (VI) described above,
to lead, after separation of the mono- and diacylated compounds, to the compound of formula:

$$\begin{bmatrix} -O-CO-R_1 \\ -OH \\ -O-CO-R'_3 \end{bmatrix} \qquad (VII)$$

in which $R_1$ and $R'_3$ have the same meaning as above, which is reacted with one equivalent of the acid chloride of formula (VIII) in the presence of a base:

$$R_2-CO-Cl \qquad (VIII)$$

to lead to the compound of formula (I/b), a particular case of the compounds of formula (I), $$\begin{bmatrix} -O-CO-R_1 \\ -O-CO-R_2 \\ -O-CO-R'_3 \end{bmatrix} \qquad (I/b)$$

in which $R_1$, $R_2$ and $R'_3$ have the same meaning as above, which compounds of formula (I/a) or (I/b), when $R'_3$ represents a 2-methyl-5-pyrazinyl radical, can be subjected to an oxidation with hydrogen peroxide in acetic medium, to lead respectively to the compounds of formula (I/c) and (I/d), particular cases of the compounds of formula (I):

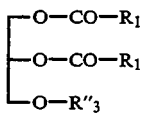
(I/c)

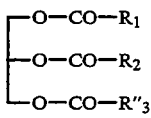
(I/d)

in which $R_1$ and $R_2$ have the same meaning as in formula (I) and $R''_3$ represents a 2-methyl-5-pyrazinyl N-oxide radical, which compounds of formula (I/a), (I/b), (I/c) or (I/d):

are purified, if appropriate, according to a standard purification technique, whose isomers, if desired, are separated according to a standard purification technique, and are optionally converted to their addition salts with a pharmaceutically acceptable acid.

The compounds of formula (I) in which $R_1=R_2$ can also be obtained according to the process wherein a compound of formula (IX), in the racemic form or the form of a pure enantiomer (obtained according to the process described by F. R. Pfeiffer et al., Tet. Lett., 32, 3549–3552, 1968):

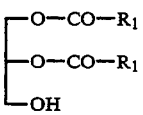
(IX)

in which $R_1$ has the same meaning as in formula (I), is reacted with the acid chloride of formula (III), in the presence of a base:

$R'_3$—CO—Cl (III)

in which $R'_3$ represents a 3-pyridyl or 2-methyl- 5-pyrazinyl radical, to lead to the compound of formula (I/a), a particular case of the compounds of formula (I):

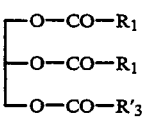
(I/a)

in which $R_1$ and $R'_3$ have the same meaning as above, which compound of formula (I/a), when $R'_3$ represents a 2-methyl-5-pyrazinyl radical, can be subjected to an oxidation with hydrogen peroxide in acetic medium to lead to the compound of formula (I/c), a particular case of the compounds of formula (I)

(I/c)

in which $R_1$ has the same meaning as in formula (I) and $R''_3$ represents a 2-methyl-5-pyrazinyl N-oxide radical, which compound of formula (I/a) or (I/c)

is purified, if appropriate, according to a standard purification technique, whose isomers, if desired, are separated according to a standard purification technique, and is optionally converted to its addition salt with a pharmaceutically acceptable acid.

These new diacylglycerol nicotinates have very advantageous pharmacological properties. In particular, they reduce the concentration of plasma lipids and, for this reason, can be used in the prevention of atherosclerosis. Compared with the known nicotinates, these new products prevent the early peak of initial nicotinic acid concentration and do not lead to the resurgence effect.

The invention also applies to the pharmaceutical compositions containing, as active principle, at least one compound of formula (I) or its optical isomers with one or a number of inert, nontoxic and suitable excipients. The pharmaceutical compositions thus obtained can be provided in various forms, the most advantageous being tablets, sugar-coated tablets, gelatin capsules, suppositories, drinkable suspensions, transdermal forms (gel, patch), and the like.

The useful dose can be varied depending on the nature and the severity of the ailment, the administration route and depending on the age and the weight of the patient. This unit dose varies from 0.5 g to 5 g per day taken once or a number of times.

The following examples illustrate the invention and do not limit it in any way.

The starting materials used are known substances or prepared according to known procedures.

EXAMPLE 1

Glycerol 1,2-distearate-3-nicotinate

Stage A: Glycerol 1,2-isopropylidene-3-nicotinate

To a solution maintained at 0° C., with stirring, containing 80 mmol of glycerol 1,2-isopropylidene in 100 ml of chloroform are added, dropwise, 160 mmol of triethylamine and then 80 mmol of nicotinoyl chloride hydrochloride. After stirring for 12 hours at 20° C., the mixture is diluted with 300 ml of ethyl ether and then washed with 100 ml of water, 100 ml of a 5% aqueous sodium bicarbonate solution and again with 100 ml of water. The organic phase is dried and concentrated under vacuum.

The expected product is obtained, in the form of an oil, after purification of the residue by chromatography on silica gel, dichloromethane being used as eluent.

Boiling point: 148°–150° C. (p=26.66 Pa)

Stage B: Glycerol 3-nicotinate

A suspension containing 21 mmol of the product obtained in the preceding stage in 30 ml of 10% aqueous acetic acid is heated for 3 hours at 100° C. After cooling and concentrating, the oily residue obtained is purified by chromatography on silica gel, using a dichloromethane/methanol (93/7) mixture as eluent, and leads to the expected product in the form of a white solid.
Melting point: 87°–88° C.

Stage C: Glycerol 1,2-distearate-3-nicotinate

A solution containing 24 mmol of stearoyl chloride in 30 ml of chloroform is added dropwise and with stirring to a solution cooled to 0° C. containing 12 mmol of the product obtained in the preceding stage and 24 mmol of pyridine in 30 ml of chloroform. The reaction mixture is stirred at 20° C. overnight and then washed with water, dried and evaporated under vacuum. The oily residue obtained is purified by chromatography on silica gel, using a dichloromethane/acetone (98/2) mixture as eluent, and leads to the expected product in the form of a white solid after recrystallization from hexane.
Melting point: 67°–69° C.

Elemental microanalysis:

|  | C% | H% | N% |
|---|---|---|---|
| Calculated | 74.03 | 10.91 | 1.92 |
| Found | 74.06 | 10.72 | 2.07 |

The following examples were obtained using the same procedure as that described for Example 1.

EXAMPLE 2

Glycerol 1,2-dimyristate-3-nicotinate

Melting point: 49°–51° C. (hexane)

Elemental microanalysis:

|  | C% | H% | N% |
|---|---|---|---|
| Calculated | 71.92 | 10.28 | 2.27 |
| Found | 71.99 | 10.49 | 2.38 |

EXAMPLE 3

Glycerol 1,2-dipalmitate-3-nicotinate

Melting point: 64°–66° C. (hexane)

Elemental microanalysis:

|  | C% | H% | N% |
|---|---|---|---|
| Calculated | 73.06 | 10.62 | 2.08 |
| Found | 72.99 | 10.54 | 2.13 |

EXAMPLE 4

Glycerol (d)-1,2-dipalmitate-3-nicotinate 15.8 mmol of triethylamine, 0.4 mmol of dimethylaminopyridine and 7.9 mmol of nicotinoyl chloride hydrochloride are added successively to a solution, maintained at 0° C., containing 5.27 mmol of glycerol (d)-1,2-dipalmitate (prepared according to the process described in Tet. Lett., 32, 3549–3559, 1968) in 50 ml of chloroform. After stirring for 12 hours at 20° C., the reaction mixture is washed with water, dried and concentrated. The residue obtained is purified by chromatography on a silica column, using a dichloromethane/acetone (98/2) mixture as eluent, and leads to the expected product which is recrystallized from hexane.
Melting point: 64–66° C. Optical rotation: $[\alpha]_D^{20} = +1.2°$ (c=1%, CHCl$_3$)

Elemental microanalysis:

|  | C% | H% | N% |
|---|---|---|---|
| Calculated | 73.06 | 10.62 | 2.08 |
| Found | 73.31 | 10.26 | 2.18 |

EXAMPLE 5

Glycerol (1)-1,2-dipalmitate-3-nicotinate

This compound was obtained using the same process as that described in Example 4 from glycerol (1)-1,2-dipalmitate.
Melting point: 64°–66° C. Optical rotation: $[\alpha]_D^{20} = -1.2°$ (c=1%, CHCl$_3$)

Elemental microanalysis:

|  | C% | H% | N% |
|---|---|---|---|
| Calculated | 73.06 | 10.62 | 2.08 |
| Found | 73.29 | 10.70 | 2.22 |

Pharmacological Study of the Derivatives of the Invention

EXAMPLE 6

Study of the Reduction in the Concentration of Plasma Lipids a This study was carried out on male SDCD rats aged 10 weeks, weighing from 325 to 350 g, acclimatized for approximately ten days and not fed the day before the experiment. Administration of the products is carried out by force-feeding with an esophageal probe, each animal receiving 2 ml/kg of a 0.4 mM/kg suspension of active product in Senegal gum (20% in distilled water).

The animals are sacrificed by decapitation 30 minutes, 1 hour, 2 hours, 4 hours, 6 hours and 8 hours after administration. The parameters measured are the levels of triglycerides and of free fatty acids as well as the blood concentration of nicotinic acid.

Figure 1:
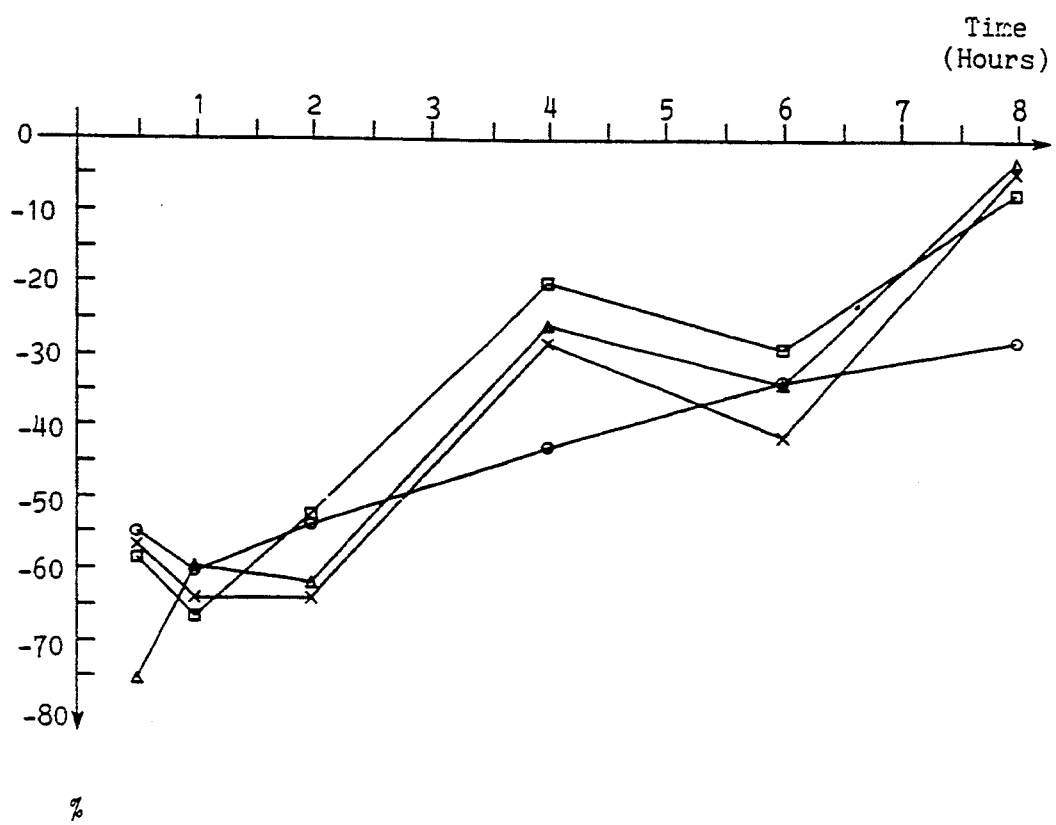
FIGS. 1 and 2 respectively show the effectiveness of the products of the invention with regard to triglycerides and the blood concentration of nicotinic acid.
Figure 2:
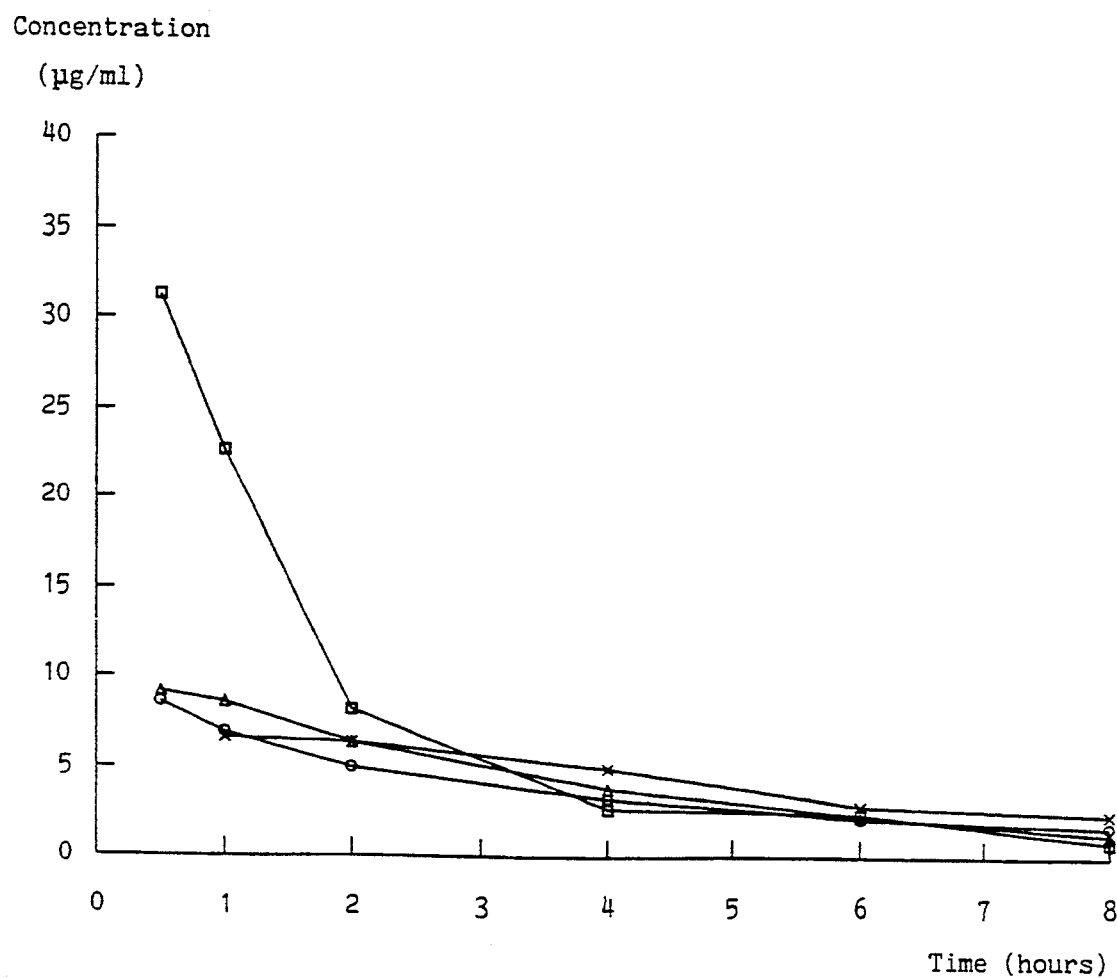
Figure 3:
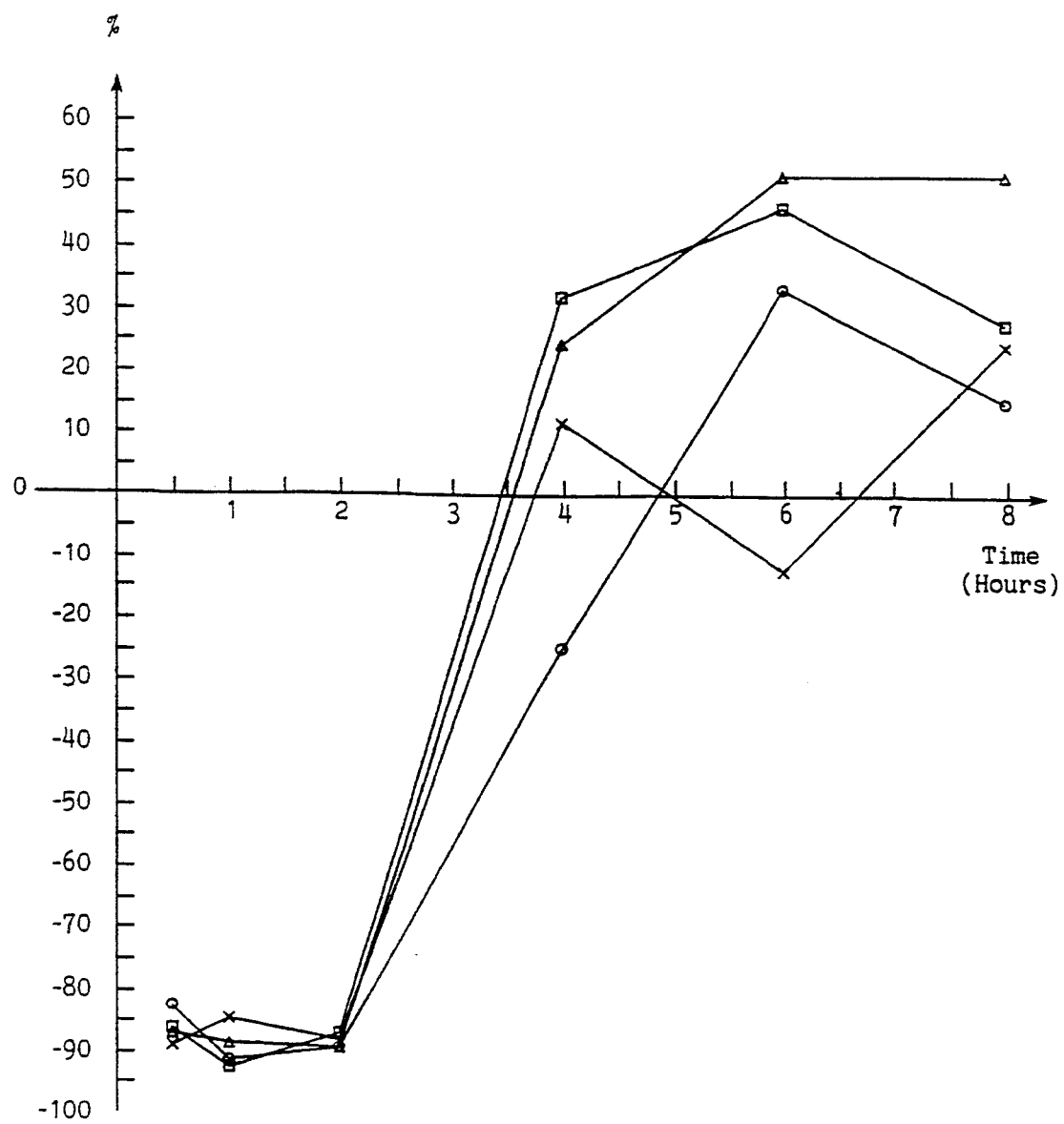
FIG. 3 shows the effect of the products of the invention with regard to free fatty acids and reveals the absence of the resurgence effect, especially for the compound of Example 1.

b Tables below show the triglycerides and free fatty acids concentrations obtained after the administration of the compound of example 3 and of its two enantiomers (examples 4 and 5), at the study was carried out with batches of 12 animals.

| Time (hours) | 1 | 2 | 4 | 6 | 8 |
|---|---|---|---|---|---|
| Level of triglycerides (mg/l) | | | | | |
| Senegal gum controls | 539 ± 49 | 598 ± 49 | 652 ± 47 | 508 ± 32 | 495 ± 49 |
| Nicotinic acid | 190 ± 19 | 498 ± 60 | 568 ± 25 | 533 ± 40 | 623 ± 51 |
| Example 3 | 192 ± 22 | 263 ± 30 | 462 ± 43 | 466 ± 33 | 503 ± 28 |

| Time (hours) | 1 | 2 | 4 | 6 | 8 |
|---|---|---|---|---|---|
| -continued | | | | | |
| Example 4 | 183 ± 22 | 238 ± 29 | 478 ± 58 | 528 ± 58 | 499 ± 25 |
| Example 5 | 196 ± 24 | 279 ± 31 | 398 ± 48 | 545 ± 33 | 544 ± 18 |
| Level of free fatty acids (mmol/l) | | | | | |
| Senegal gum controls | 0.727 ± 0.031 | 0.803 ± 0.054 | 0.833 ± 0.061 | 0.859 ± 0.050 | 0.948 ± 0.052 |
| Nicotinic acid | 0.101 ± 0.010 | 1.207 ± 0.100 | 1.068 ± 0.069 | 0.974 ± 0.078 | 1.026 ± 0.094 |
| Example 3 | 0.111 ± 0.014 | 0.265 ± 0.095 | 1.068 ± 0.059 | 1.117 ± 0.068 | 1.194 ± 0.076 |
| Example 4 | 0.133 ± 0.026 | 0.257 ± 0.052 | 1.118 ± 0.103 | 1.163 ± 0.062 | 1.040 ± 0.077 |
| Example 5 | 0.105 ± 0.026 | 0.363 ± 0.082 | 1.051 ± 0.072 | 1.240 ± 0.085 | 1.130 ± 0.055 |

EXAMPLE 7

Pharmaceutical Composition

Preparation formula for 1000 tablets containing a dose of 0.5 g

| | |
|---|---|
| Glycerol 1,2-distearate-3-nicotinate | 500 g |
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

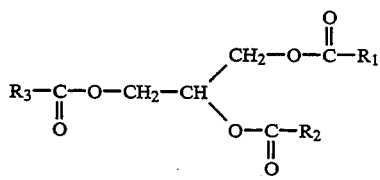

in which:

$R_1$ and $R_2$, which are identical or different, represent linear or branched ($C_{11}$–$C_{19}$) alkyl or linear or branched ($C_{11}$–$C_{19}$) alkenyl, $R_3$ represents 3-pyridyl, 2-methyl-5-pyrazinyl or 2-methyl-5-pyrazinyl N-oxide, or its enantiomers or optional diastereoisomers, or its addition salt with a pharmaceutically-acceptable acid.

2. A compound of claim 1, wherein $R_1$ and $R_2$ are identical.

3. A compound of claim 1 or 2, wherein $R_1$ and $R_2$ represent linear or branched ($C_{11}$–$C_{19}$) alkyl.

4. A compound of claim 1, wherein $R_3$ represents 3-pyridyl.

5. The compound of claim 1, which is selected from glycerol 1,2-dipalmitate-3-nicotinate and its enantiomers.

6. A method for treating a mammal afflicted with atherosclerosis comprising the step of administering to the mammal an amount of a compound of claim 1 which is effective for alleviation of said condition.

7. A pharmaceutical composition useful in combating atherosclerosis comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,385,920
DATED : January 31, 1995
INVENTOR(S) : Alex Cordi, Jean-Michel Lacoste, Jacques Duhault, Joseph Espinal, Michelle Boulanger It is certified that error appears in the above-indentified patent and that said Letters Patent is hereby corrected as shown below:

Column 3, the formula (I/c) between lines 10 and 15; last line of formula, "O—R''$_3$" should read -- O—CO—R''$_3$ --
Column 8, line 15; insert a comma "," between the words "pyrazinyl" and "or"

Signed and Sealed this

Sixteenth Day of May, 1995

Attest:

BRUCE LEHMAN

Attesting Officer    Commissioner of Patents and Trademarks